US012697076B2

(12) United States Patent
Siejko et al.

(10) Patent No.: US 12,697,076 B2
(45) Date of Patent: Aug. 4, 2026

(54) SYSTEMS AND METHODS FOR DETECTING PREMATURE VENTRICULAR CONTRACTION

(71) Applicant: Cardiac Pacemakers, Inc., St. Paul, MN (US)

(72) Inventors: Krzysztof Z. Siejko, Maple Grove, MN (US); Abhijit Rajan, Shoreview, MN (US); Alicia Elaine Byrnes, Shoreview, MN (US); Matthew James Fuhs, Anoka, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 284 days.

(21) Appl. No.: 18/218,504

(22) Filed: Jul. 5, 2023

(65) Prior Publication Data

US 2024/0008821 A1     Jan. 11, 2024

Related U.S. Application Data

(60) Provisional application No. 63/359,338, filed on Jul. 8, 2022.

(51) Int. Cl.
| | |
|---|---|
| *A61B 5/00* | (2006.01) |
| *A61B 5/0245* | (2006.01) |
| *A61B 5/352* | (2021.01) |

(52) U.S. Cl.
CPC .......... *A61B 5/7275* (2013.01); *A61B 5/0245* (2013.01); *A61B 5/352* (2021.01); *A61B 5/6847* (2013.01)

(58) Field of Classification Search
None
See application file for complete search history.

(56) References Cited

U.S. PATENT DOCUMENTS

| | | |
|---|---|---|
| 11,202,599 B2 | 12/2021 | Saha et al. |
| 2016/0310031 A1* | 10/2016 | Sarkar .................... A61B 5/686 |

(Continued)

FOREIGN PATENT DOCUMENTS

EP     3965878 A1     3/2022

OTHER PUBLICATIONS

Chazal, P., "Automatic Classification of Heartbeats Using ECG Morphology and Heartbeat Interval Features", IEEE Trans. on Biomed Eng. 51:7, Jul. 2004, 1196-1206.

(Continued)

*Primary Examiner* — Ankit D Tejani
(74) *Attorney, Agent, or Firm* — Nelson Mullins Riley & Scarborough LLP

(57)     ABSTRACT

Systems and methods for detecting and classifying premature ventricular contractions (PVCs) are discussed. An exemplary system includes a sensor circuit to sense a cardiac signal of a subject, and a processor circuit to detect heartbeats from the cardiac signal and detect a PVC under a first detection mode or a different second detection mode. The first detection mode includes identifying a PVC candidate of a particular type using cardiac intervals or signal amplitudes of the detected heartbeats, and classifying the identified PVC candidate as a PVC singleton or a pattern of multiple consecutive PVCs using signal features including morphology features of the sensed cardiac signal. The second detection mode includes detecting PVC of the particular type using the cardiac intervals or the signal amplitudes of the detected heartbeats. The first detection mode can be transitioned to the second detection mode in response to a mode-switching trigger event.

20 Claims, 7 Drawing Sheets

(56)     References Cited

U.S. PATENT DOCUMENTS

| | | |
|---|---|---|
| 2020/0357519 A1 | 11/2020 | Chakravarthy et al. |
| 2021/0128005 A1* | 5/2021 | Burnes ................. A61B 5/6869 |
| 2021/0275081 A1* | 9/2021 | May ....................... A61B 5/341 |
| 2021/0338134 A1 | 11/2021 | Chakravarthy et al. |

OTHER PUBLICATIONS

Christov, Ivaylo, et al., "Comparative study of morphological and time-frequency ECG descriptors for heartbeat classification", Medical Engineering & Physics 28 (2006) 876-887.

Krasteva, Vessela, et al., "QRS Template Matching for Recognition of Ventricular Ectopic Beats", Annals of Biomedical Engineering, vol. 35, No. 12, Dec. 2007, pp. 2065-2076.

Lustgarten, Daniel L., et al., "Premature ventricular contraction detection for long-term monitoring in an implantable cardiac monitor", https://doi.org/10.1111/pace.13903, date unknown.

International Preliminary Report on Patentability received for PCT Patent Application No. PCT/US2023/026907, mailed on Jan. 23, 2025, 9 pages.

International Search Report and Written Opinion received for PCT Patent Application No. PCT/US2023/026907, mailed on Oct. 11, 2023, 10 pages.

* cited by examiner

SYSTEMS AND METHODS FOR DETECTING PREMATURE VENTRICULAR CONTRACTION

This application claims the benefit of U.S. Provisional Application No. 63/359,338, filed on Jul. 8, 2022, which is hereby incorporated by reference in its entirety.

TECHNICAL FIELD

This document relates generally to medical devices, and more particularly, to systems, devices, and methods for detecting various types of premature ventricular contractions (PVCs).

BACKGROUND

Implantable medical devices (IMDs) have been used for monitoring patient health condition or disease states and delivering therapies. For example, implantable cardioverter-defibrillators (ICDs) may be used to monitor for certain abnormal heart rhythms and to deliver electrical energy to the heart to correct the abnormal rhythms. Some IMDs may be used to monitor for chronic worsening of cardiac hemo-dynamic performance, such as due to congestive heart failure (CHF), and to provide cardiac stimulation therapies, including cardiac resynchronization therapy (CRT) to correct cardiac dyssynchrony within a ventricle or between ventricles.

Some IMDs can detect cardiac arrhythmia. One common type of cardiac arrhythmia is premature ventricular contractions (PVCs), also known as ventricular premature beats or ventricular extrasystoles. A PVC is a too-early heartbeat that originates in the ventricles and disrupts the heart's normal rhythm. A typical PVC pattern includes a normal beat, an extra beat (the PVC), a slight pause, then a stronger-than-normal beat, although other PVC patterns can also be identified clinically in patients. The heart fills with more blood during the pause following the PVC, giving the next beat extra force. PVCs may occur randomly or regularly such as at definite intervals. PVCs may be concentrated in periods of high density or spread uniformly throughout the day.

PVCs can occur in isolation or in repeated patterns. When a PVC occurs as a single premature beat (also referred to as a single PVC, or a PVC singleton), patients may describe the feeling as a "palpitation" or "skipped beat." The beat following the PVC can be strong enough to cause pain or discomfort in the chest. The most commonly encountered single PVC pattern may include a prolonged compensatory pause post the PVC. If the PVCs continuously alternate with a regular sinus beat, the patient is in bigeminy. Likewise, if every third heartbeat is a PVC, then it is named trigeminy. Some PVCs may occur as a PVC couplet pattern, characterized by two consecutive PVCs. The two PVCs in a PVC couplet may arise from the same ectopic focus (unifocal PVCs), or from two or more ectopic foci (multifocal PVCs). A pattern of three or more (but less than a threshold number, such as thirty in an example) consecutive PVCs is referred to as a PVC run, or a non-sustained ventricular tachycardia (NSVT).

PVCs can be associated with various cardiac or non-cardiac pathologies. Examples include cardiomyopathy, mitral valve prolapse, and myocardial infarction. Any structural heart disease that alters conduction pathways due to tissue alterations can cause PVCs. Non-cardiac examples are hyperthyroidism, anemia, and even hypertension. Patient populations with higher risks of cardiovascular disease and clinically poor cardiovascular markers have a higher occurrence of PVC.

Individuals who have frequent PVCs or a series of them may experience a fluttering sensation in the chest or neck. If PVCs are frequent enough to reduce the heart's pumping ability, the individual may experience weakness, dizziness or fainting. A PVC burden is a quantitative measure of the frequency PVCs in a patient, and can be calculated as the percentage of all ventricular beats that are PVCs of any types (singleton, couplets, or NSVT) measured over a specified period of time, typically 24 hours. Although a PVC burden less than ~5% is generally considered benign, a PVC burden exceeding 10-20% may be clinically actionable. Accurate and efficient detection of PVCs of various types can help improve PVC burden estimate and appropriate management of patients with cardiac arrhythmias.

Overview

Timely detection of PVCs and recognition of PVC types or patterns may be clinically important for an accurate estimate of a patient's PVC burden and for clinical evaluation of cardiac function. Conventional PVC detection and PVC burden estimation are focused on detecting single PVCs (PVC singletons) based on a characteristic interval pattern, such as a shorter (than a cardiac cycle during normal sinus rhythm) pre-PVC interval followed by a prolonged compensatory pause. Such conventional methods have several disadvantages. First, although most single PVCs are characterized by a prolonged post-PVC compensatory pause, in some patients or in certain cases, a single PVC may not be accompanied by a compensatory pause, especially when a PVC is fast enough so that the next sinus beat is conducted normally, or during certain atrial arrhythmias such as atrial fibrillation. Detections relied upon prolonged compensatory pause may miss some single PVCs, and reduce the accuracy of PVC burden estimate. Second, interval-based PVC detection algorithm may produce false detections (including false positive or false negative detections), which may also reduce the accuracy of PVC burden estimate. Although more sophisticated features such as signal morphology can be used to detect single PVCs, detection algorithms using such features typically require more computational resources. Morphology analysis of every single heartbeat may not be feasible in a resource and power conservative environment, such as real-time PVC detection by a battery-powered implantable device. Third, conventional PVC detection techniques, which focus on detecting single PVCs, are generally not designed or optimized for detecting other PVC types of patterns such as PVC couplet or runs of three or more PVCs. Although the same single PVC detection algorithm may be used to detect other PVC patterns, such an approach can be less efficient, and generally puts a high demand for computational resources particularly in real-time implementations. More importantly, as single PVCs and PVC couplets or PVC runs generally have different characteristics (e.g., interval patterns such as compensatory pause, PVC morphologies, etc.), an algorithm designed or optimized for detecting single PVCs may cause false positive or false negative detection of PVC beats in a couplet or PVC run, and thus reduce the accuracy of PVC burden estimate.

This document discusses, among other things, systems, devices, and methods for detecting and classifying PVCs of various types. An exemplary system includes a sensor circuit to sense a cardiac signal of a subject, and a processor circuit to detect heartbeats from the sensed cardiac signal, and to detect a PVC under a first detection mode or a different second detection mode. Under the first detection mode, the processor circuit can identify a PVC candidate of a particular type using cardiac intervals or signal amplitudes of the detected heartbeats. The PVC candidate can be one of a PVC singleton candidate, a PVC couplet candidate, or a PVC run candidate. The processor circuit can generate a set of signal features including morphology features from the sensed cardiac signal, and classify the identified PVC candidate as a PVC singleton or a pattern of multiple consecutive PVCs using the generated set of signal features. Under the second detection mode, the processor circuit can detect the PVC of the particular type using the cardiac intervals or the signal amplitudes of the detected heartbeats. The first detection mode can be transitioned to the second detection mode in response to a mode-switching trigger event. The processor circuit can determine a PVC burden based on the detected PVCs.

Example 1 is an implantable medical device for detecting cardiac arrhythmia in a subject, comprising: a sensor circuit configured to sense a cardiac signal of the subject; and a processor circuit configured to: detect heartbeats from the sensed cardiac signal; detect a premature ventricular contraction (PVC) under a first detection mode, including to: identify a PVC candidate of a particular type using cardiac intervals or signal amplitudes of the detected heartbeats; generate a set of signal features including morphology features from the sensed cardiac signal; and classify the identified PVC candidate as a PVC singleton or a pattern of multiple consecutive PVCs using the generated set of signal features; and in response to a mode-switching trigger event, detect the PVC of the particular type under a second detection mode different than the first detection mode using the cardiac intervals or the signal amplitudes of the detected heartbeats.

In Example 2, the subject matter of Example 1 optionally includes, wherein the mode-switching trigger event includes a passage of a threshold time after the detection of PVC under the first detection mode.

In Example 3, the subject matter of Example 2 optionally includes, wherein the threshold time is a number of weeks.

In Example 4, the subject matter of any one or more of Examples 1-3 optionally include, wherein the processor circuit is configured to determine a PVC burden representing a percentage of heartbeats being detected as the PVC singleton or the pattern of multiple consecutive PVCs.

In Example 5, the subject matter of any one or more of Examples 1-4 optionally include, wherein the first detection mode includes at least one trained computational model including respective weight factors for the set of signal features, the at least one trained computational model being trained to recognize one or more PVC types.

In Example 6, the subject matter of Example 5 optionally includes, wherein the at least one trained computational model includes a logistic regression model, wherein to classify the identified PVC candidate under the first detection mode, the processor circuit is configured to: compute a weighted combination of the generated set of signal features each weighted by the respective weight factors; and classify the identified PVC candidate as the PVC singleton or the pattern of multiple consecutive PVCs based on a comparison of the weighted combination to a confidence threshold.

In Example 7, the subject matter of any one or more of Examples 5-6 optionally include, wherein the pattern of multiple consecutive PVCs includes a PVC couplet or a PVC run of three or more consecutive PVCs; wherein the identified PVC candidate includes one or more of an identified PVC singleton candidate, an identified PVC couplet candidate, or an identified PVC run candidate, wherein the at least one trained computational model includes one or more of a trained singleton detection model, a trained couplet detection model, or a trained PVC run detection model, wherein to classify the identified PVC candidate, the processor circuit is configured to apply the trained singleton detection model to the identified PVC singleton candidate, apply the trained couplet detection model to the identified PVC couplet candidate, or to apply the trained PVC run detection model to the identified PVC run candidate.

In Example 8, the subject matter of Example 7 optionally includes, wherein the processor circuit is configured to: identify the PVC candidate as the PVC singleton candidate; and apply the sensed cardiac signal to the trained singleton detection model to generate a singleton feature set for the identified PVC singleton candidate, and to confirm a PVC singleton detection using the singleton feature set and the trained singleton detection model.

In Example 9, the subject matter of Example 8 optionally includes, wherein the processor circuit is configured to, in response to the confirmed PVC singleton detection, apply the sensed cardiac signal to a trained post-singleton PVC detection model to generate a post-singleton feature set for a heartbeat immediately following the confirmed PVC singleton, and to confirm a PVC couplet detection using the post-singleton feature set and the trained post-singleton PVC detection model.

In Example 10, the subject matter of Example 7 optionally includes, wherein the processor circuit is configured to: identify the PVC candidate as the PVC couplet candidate based on two consecutive cardiac intervals shorter than an interval threshold; and apply the sensed cardiac signal to the trained couplet detection model to generate first and second feature sets respectively for the two consecutive PVCs of the identified PVC couplet candidate, and to confirm a PVC couplet detection using the first and second feature sets and the trained couplet detection model.

In Example 11, the subject matter of Example 7 optionally includes, wherein the processor circuit is configured to: identify the PVC candidate as the PVC run candidate based on (i) three or more consecutive cardiac intervals shorter than an interval threshold, or (ii) a confirmed PVC couplet detection; and apply the sensed cardiac signal to the trained PVC run detection model to generate a third feature set for a third or subsequent PVC of the PVC run candidate, and to confirm a PVC run detection using the third feature set and the trained PVC run detection model.

In Example 12, the subject matter of any one or more of Examples 1-11 optionally include, wherein the set of signal features generated under the first detection mode include: one or more amplitude features including a ratio of a peak-to-peak (PP) amplitudes between two consecutive heartbeats in the sensed cardiac signal; or one or more interval features including a difference of cardiac intervals between two consecutive heartbeats in the sensed cardiac signal.

In Example 13, the subject matter of any one or more of Examples 1-12 optionally include, wherein the set of signal features generated under the first detection mode include one or more morphology features including: a first morphological similarity metric between (i) a heartbeat in the sensed cardiac signal and (ii) a normal sinus rhythm (NSR) morphology; or a second morphological similarity metric between two consecutive heartbeats in the sensed cardiac signal.

In Example 14, the subject matter of Example 13 optionally includes, wherein one or more of the first or the second morphological similarity metric includes a correlation metric.

In Example 15, the subject matter of any one or more of Examples 13-14 optionally include, wherein the processor circuit is configured to: detect a change in NSR morphology; and classify the identified PVC candidate using the first morphological similarity metric and the second morphological similarity metric if the detected change in NSR morphology is below a change threshold, and using the second morphological similarity metric but not the first morphological similarity metric if the detected change in NSR morphology exceeds the change threshold.

Example 16 is a method for detecting cardiac arrhythmia in a subject using an implantable medical device, comprising: sensing a cardiac signal of the subject using a sensor circuit; detecting heartbeats from a cardiac signal of the subject; detecting a premature ventricular contraction (PVC) under a first detection mode, including: identifying a PVC candidate of a particular type using cardiac intervals or signal amplitudes of the detected heartbeats; generating a set of signal features including morphology features from the sensed cardiac signal; and classifying the identified PVC candidate as a PVC singleton or a pattern of multiple consecutive PVCs using the generated set of signal features; in response to a mode-switching trigger event, detecting the PVC of the particular type under a second detection mode different than the first detection mode using the cardiac intervals or the signal amplitudes of the detected heartbeats.

In Example 17, the subject matter of Example 16 optionally includes, wherein the mode-switching trigger event includes a passage of a threshold time after the detection of PVC under the first detection mode.

In Example 18, the subject matter of any one or more of Examples 16-17 optionally include, wherein the first detection mode includes at least one trained computational model including respective weight factors for the set of signal features, the at least one trained computational model being trained to recognize one or more PVC types.

In Example 19, the subject matter of Example 18 optionally includes, wherein the pattern of multiple consecutive PVCs includes a PVC couplet or a PVC run of three or more consecutive PVCs, wherein the identified PVC candidate includes one or more of an identified PVC singleton candidate, an identified PVC couplet candidate, or an identified PVC run candidate, wherein the at least one trained computational model includes one or more of a trained singleton detection model, a trained couplet detection model, or a trained PVC run detection model, wherein classifying the identified PVC candidate includes applying the trained singleton detection model to the identified PVC singleton candidate, applying the trained couplet detection model to the identified PVC couplet candidate, or applying the trained PVC run detection model to the identified PVC run candidate.

In Example 20, the subject matter of Example 19 optionally includes: identifying the PVC candidate as the PVC singleton candidate; applying the cardiac signal to the trained singleton detection model to generate a singleton feature set for the identified PVC singleton candidate, and to confirm a PVC singleton detection using the singleton feature set and the trained singleton detection model; and in response to the confirmed PVC singleton detection, applying the cardiac signal to a trained post-singleton PVC detection model to generate a post-singleton feature set for a heartbeat immediately following the confirmed PVC singleton, and to confirm a PVC couplet detection using the post-singleton feature set and the trained post-singleton PVC detection model.

In Example 21, the subject matter of any one or more of Examples 19-20 optionally include: identifying the PVC candidate as the PVC couplet candidate based on two consecutive cardiac intervals shorter than an interval threshold; and applying the cardiac signal to the trained couplet detection model to generate first and second feature sets respectively for the two consecutive PVCs of the identified PVC couplet candidate, and to confirm a PVC couplet detection using the first and second feature sets and the trained couplet detection model.

In Example 22, the subject matter of any one or more of Examples 19-21 optionally include: identifying the PVC candidate as the PVC run candidate based on one or more of (i) three or more consecutive cardiac intervals shorter than an interval threshold or (ii) a confirmed PVC couplet detection; and applying the cardiac signal to the trained PVC run detection model to generate a third feature set for a third or subsequent PVC of the PVC run candidate, and to confirm a PVC run detection using the third feature set and the trained PVC run detection model.

Embodiments of systems, devices, and methods discussed in this document may improve the technology of device-based arrhythmia detection, particularly detection of PVCs and estimation of PVC burden. According to some embodiments, multiple PVC detectors can be tailored for detecting or classifying different PVC types (patterns) such as PVC singleton, couplets, or PVC runs using respectively optimized feature sets. In some examples, the dedicated detectors can each be implemented as respective computational models individually trained to optimize their performances for detecting a PVC pattern. In some examples, the feature set used by a detector can be dynamically determined based on, for example, patient physiological or physical condition (e.g., posture or physical activity state). Compared to conventional PVC detector that focuses on detecting single PVCs, the dedicated detectors as described in this document can help reduce false positive and false negative detections or classifications of PVC patterns such as couplets or PVC runs, thereby improving overall accuracy of PVC burden estimate. Additionally, the dedicated couplet and PVC run detectors can be more accurate and efficient than applying the same single PVC detection algorithm to detect each and every PVC beats in a PVC couplet or PVC run, particularly in an energy and resource conscious system, such as an implantable medical device.

According to some examples, a tiered PVC detection involves a first trigger stage to flag a PVC candidate (either a singleton candidate, or a couplet or PVC run candidate) using only cardiac intervals or signal amplitude information, and a second confirmation stage to confirm and classify the identified PVC candidate using more sophisticated features (e.g., morphology features) and algorithms than the first trigger stage. Because the first trigger stage requires less resources, PVC candidates can be more efficiently identified; and the system resources can be better utilized by the second confirmation stage to more precisely detect and classify the PVC into different types such as PVC singleton, couplets, or PVC runs. As such, compared to conventional PVC detection techniques, the tiered PVC detection as discussed in this document can not only improve PVC detection and classification performance (e.g., higher sensitivity and specificity) and PVC burden estimation accuracy, but also make better use of system resources, reduce power consumption to meet device longevity requirements in an implantable medical device, thereby improving the functionality of the implantable medical device.

Morphology based PVC detection generally requires more system resources and consumes more power, which makes it more challenging to meet the power consumption requirements in an implantable medical device. The present invention describes a unique technique to transition between two different PVC detection modes with different computation complexity and power requirements. The first detection mode involves the tiered PVC detection that uses computation and power intensive morphology based features. The second detection mode uses simpler features such as cardiac intervals and/or the signal amplitudes, but not morphology features. Transition between the first and second detection modes can happen in response to a mode-switching trigger event, such as a passage of a threshold time (e.g., one week, two weeks, or other specified time duration) after PVC detection under the first detection mode. Because the second detection mode generally requires less computation and power consumption than the first detection mode, automatically transitioning to the second detection model can help save battery power of an implantable medical device and extend device longevity.

The improvements in PVC detection and PVC burden estimate discussed herein may be achieved with little to no additional cost or added system complexity. In some examples, existing system performance may be maintained (e.g., high PVC detection sensitivity and specificity, etc.) using lower cost or less obtrusive systems, apparatus, and methods. With improved PVC detection, fewer alarms are provided, battery life may be extended, fewer unnecessary drugs and procedures may be scheduled, prescribed, or provided, and an overall system cost and power savings may be realized in contrast to existing medical devices and systems.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting and classifying premature ventricular contractions (PVCs) of various types. An exemplary system includes a sensor circuit to sense a cardiac signal of a subject, and a processor circuit to detect heartbeats from the cardiac signal and detect a PVC under a first detection mode or a different second detection mode. The first detection mode includes identifying a PVC candidate of a particular type using cardiac intervals or signal amplitudes of the detected heartbeats, and classifying the identified PVC candidate as a PVC singleton or a pattern of multiple consecutive PVCs using signal features including morphology features of the sensed cardiac signal. The second detection mode includes detecting PVC of the particular type using the cardiac intervals or the signal amplitudes of the detected heartbeats. Transition between the first and second detection modes can happen in response to a mode-switching trigger event.

Figure 1:
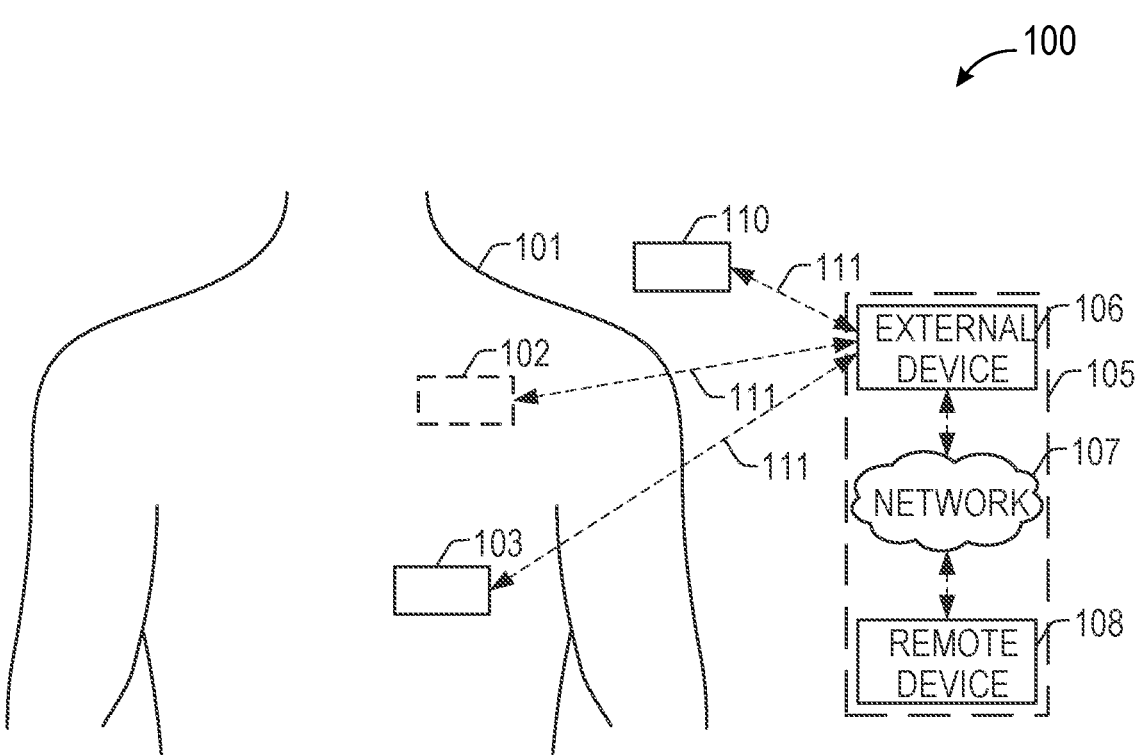
FIG. 1 illustrates generally an example of a patient management system and portions of an environment in which the system may operate.

FIG. 1 illustrates an example patient management system 100 and portions of an environment in which the patient management system 100 may operate. The patient management system 100 can perform a range of activities, including remote patient monitoring and diagnosis of a disease condition. Such activities can be performed proximal to a patient 101, such as in a patient home or office, through a centralized server, such as in a hospital, clinic, or physician office, or through a remote workstation, such as a secure wireless mobile computing device.

The patient management system 100 can include one or more ambulatory medical devices, an external system 105, and a communication link 111 providing for communication between the one or more ambulatory medical devices and the external system 105. The one or more ambulatory medical devices can include an implantable medical device (IMD) 102, a wearable medical device (WMD) 103, or one or more other implantable, leadless, subcutaneous, external, wearable, or ambulatory medical devices configured to monitor, sense, or detect information from, determine physiologic information about, or provide one or more therapies to treat various conditions of the patient 101, such as one or more cardiac or non-cardiac conditions (e.g., dehydration, sleep disordered breathing, etc.).

In an example, the IMD 102 can include one or more traditional cardiac rhythm management devices implanted in a chest of a patient, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the patient 101. In another example, the IMD 102 can include a monitor implanted, for example, subcutaneously in the chest of patient 101, the IMD 102 including a housing containing circuitry and, in certain examples, one or more sensors, such as a temperature sensor, etc.

The IMD 102 can include an assessment circuit configured to detect or determine specific physiologic information of the patient 101, or to determine one or more conditions or provide information or an alert to a user, such as the patient 101 (e.g., a patient), a clinician, or one or more other caregivers or processes. The IMD 102 can alternatively or additionally be configured as a therapeutic device configured to treat one or more medical conditions of the patient 101. The therapy can be delivered to the patient 101 via the lead system and associated electrodes or using one or more other delivery mechanisms. The therapy can include delivery of one or more drugs to the patient 101, such as using the IMD 102 or one or more of the other ambulatory medical devices, etc. In some examples, therapy can include cardiac resynchronization therapy for rectifying dyssynchrony and improving cardiac function in heart failure patients. In other examples, the IMD 102 can include a drug delivery system, such as a drug infusion pump to deliver drugs to the patient for managing arrhythmias or complications from arrhythmias, hypertension, or one or more other physiologic conditions. In other examples, the IMD 102 can include one or more electrodes configured to stimulate the nervous system of the patient or to provide stimulation to the muscles of the patient airway, etc.

The WMD 103 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.).

The external system 105 can include a dedicated hardware/software system, such as a programmer, a remote server-based patient management system, or alternatively a system defined predominantly by software running on a standard personal computer. The external system 105 can manage the patient 101 through the IMD 102 or one or more other ambulatory medical devices connected to the external system 105 via a communication link 111. In other examples, the IMD 102 can be connected to the WMD 103, or the WMD 103 can be connected to the external system 105, via the communication link 111. This can include, for example, programming the IMD 102 to perform one or more of acquiring physiological data, performing at least one self-diagnostic test (such as for a device operational status), analyzing the physiological data, or optionally delivering or adjusting a therapy for the patient 101. Additionally, the external system 105 can send information to, or receive information from, the IMD 102 or the WMD 103 via the communication link 111. Examples of the information can include real-time or stored physiological data from the patient 101, diagnostic data, such as detection of patient hydration status, hospitalizations, responses to therapies delivered to the patient 101, or device operational status of the IMD 102 or the WMD 103 (e.g., battery status, lead impedance, etc.). The communication link 111 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

The external system 105 can include an external device 106 in proximity of the one or more ambulatory medical devices, and a remote device 108 in a location relatively distant from the one or more ambulatory medical devices, in communication with the external device 106 via a communication network 107. Examples of the external device 106 can include a medical device programmer. The remote device 108 can be configured to evaluate collected patient or patient information and provide alert notifications, among other possible functions. In an example, the remote device 108 can include a centralized server acting as a central hub for collected data storage and analysis. The server can be configured as a uni-, multi-, or distributed computing and processing system. The remote device 108 can receive data from multiple patients. The data can be collected by the one or more ambulatory medical devices, among other data acquisition sensors or devices associated with the patient 101. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more ambulatory medical devices, such as the implantable medical device. By way of example, alert notifications can include a Web page update, phone or pager call, E-mail, SMS, text or "Instant" message, as well as a message to the patient and a simultaneous direct notification to emergency services and to the clinician. Other alert notifications are possible. The server can include an alert prioritizer circuit configured to prioritize the alert notifications. For example, an alert of a detected physiological event can be prioritized using a similarity metric between the physiological data associated with the detected physiological event to physiological data associated with the historical alerts.

The remote device 108 may additionally include one or more locally configured clients or remote clients securely connected over the communication network 107 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 108, including the server and the interconnected clients, may also execute a follow-up scheme by sending follow-up requests to the one or more ambulatory medical devices, or by sending a message or other communication to the patient 101 (e.g., the patient), clinician or authorized third party as a compliance notification.

The communication network 107 can provide wired or wireless interconnectivity. In an example, the communication network 107 can be based on the Transmission Control Protocol/Internet Protocol (TCP/IP) network communication specification, although other types or combinations of networking implementations are possible. Similarly, other network topologies and arrangements are possible.

One or more of the external device 106 or the remote device 108 can output the detected physiological events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 106 or the remote device 108 can include a respective display unit for displaying the physiologic or functional signals, or alerts, alarms, emergency calls, or other forms of warnings to signal the detection of arrhythmias. In some examples, the external system 105 can include an external data processor configured to analyze the physiologic or functional signals received by the one or more ambulatory medical devices, and to confirm or reject the detection of arrhythmias. Computationally intensive algorithms, such as machine-learning algorithms, can be implemented in the external data processor to process the data retrospectively to detect cardia arrhythmias.

Portions of the one or more ambulatory medical devices or the external system 105 can be implemented using hardware, software, firmware, or combinations thereof. Portions of the one or more ambulatory medical devices or the external system 105 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The therapy device 110 can be configured to send information to or receive information from one or more of the ambulatory medical devices or the external system 105 using the communication link 111. In an example, the one or more ambulatory medical devices, the external device 106, or the remote device 108 can be configured to control one or more parameters of the therapy device 110. The external system 105 can allow for programming the one or more ambulatory medical devices and can receives information about one or more signals acquired by the one or more ambulatory medical devices, such as can be received via a communication link 111. The external system 105 can include a local external implantable medical device programmer. The external system 105 can include a remote patient management system that can monitor patient status or adjust one or more therapies such as from a remote location.

Figure 2:
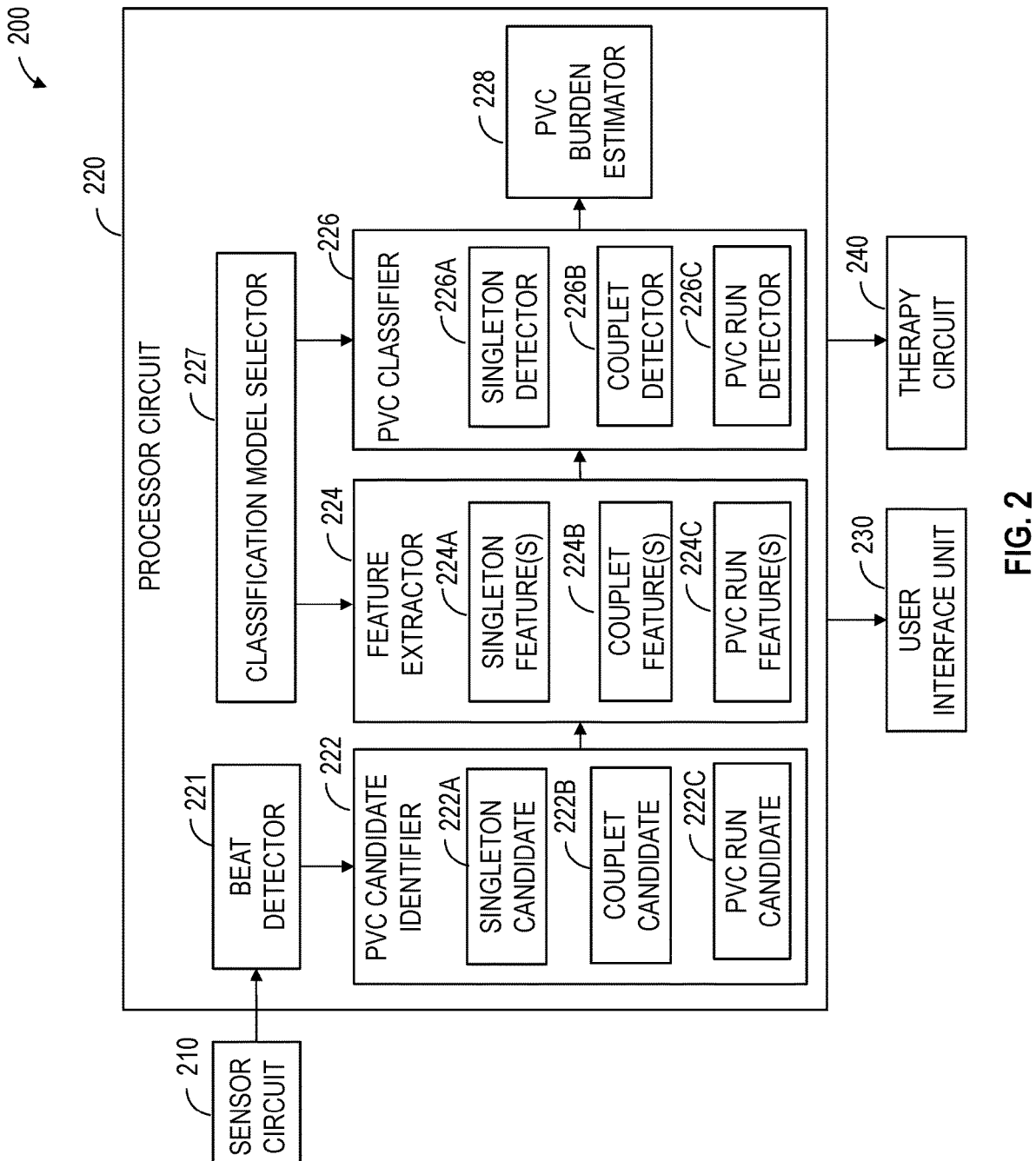
FIG. 2 illustrates generally an example of an arrhythmia detection system to detect and classify a premature ventricular contraction (PVC) and to estimate a PVC burden.

FIG. 2 illustrates generally an example of an arrhythmia detection system 200 configured to detect and classify a premature ventricular contraction (PVC) and estimate a PVC burden. Portions of the system 200 may be included in the physiologic event detector circuit 160 of the IMD 102 or the WMD 103, or the external system 105. The system 200 may include one or more of a sensor circuit 210, a processor circuit 220, and a user interface unit 230. The system 200 may additionally include an optional therapy circuit 240.

The sensor circuit 210 may include circuitry configured to sense a physiologic signal of a patient via one or more implantable, wearable, or otherwise ambulatory sensors or electrodes associated with the patient. The sensors may be incorporated into, or otherwise associated with an ambulatory device such as the IMD 102 or the WMD 103. In some examples, the sensors may be incorporated into an implantable cardiac monitor (ICM) device configured for subcutaneous implantation. Examples of the physiologic signals may include surface electrocardiography (ECG) sensed from electrodes placed on the body surface, subcutaneous ECG sensed from electrodes placed under the skin, intracardiac electrogram (EGM) sensed from the one or more electrodes on a lead system, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit 210 may include one or more sub-circuits to digitize, filter, or perform other signal conditioning operations on the received physiologic signal.

Figure 3A:
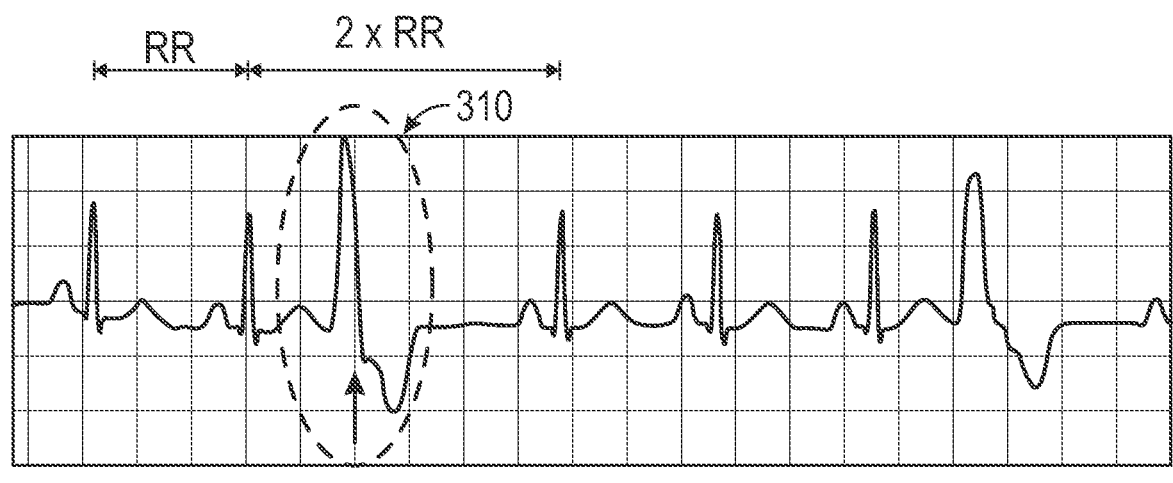
FIGS. 3A-3C illustrate example ECG tracings of various PVC types.
Figure 3B:
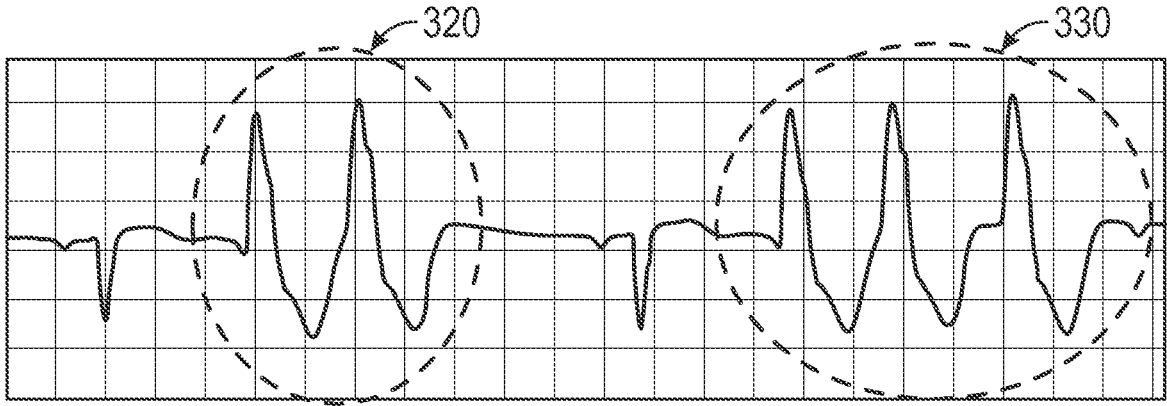
Figure 3C:
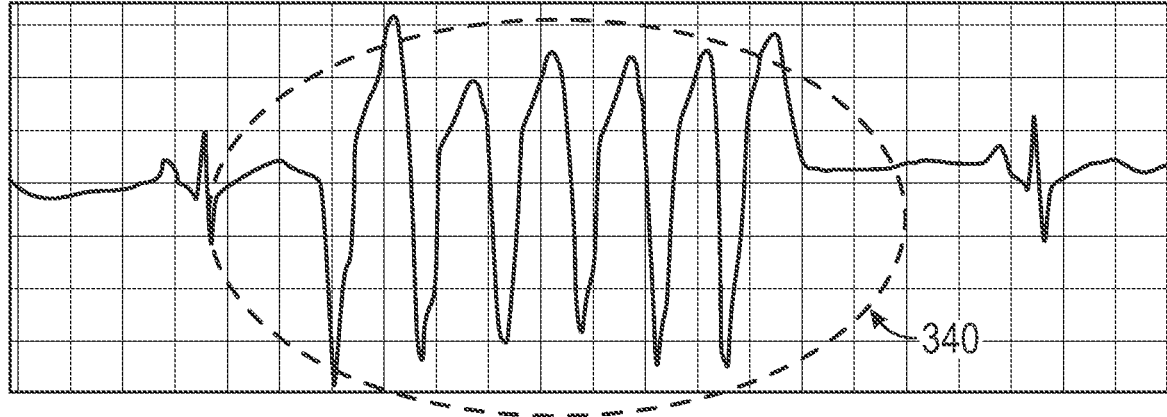

The processor circuit 220, coupled to the sensor circuit 210, may detect and classify a PVC type or pattern, such as a PVC singleton (i.e., a single PVC), a PVC couplet comprising two consecutive PVCs, or a PVC run of three or more consecutive PVCs, and determine a PVC burden estimate based on the detected and classified PVCs. FIGS. 3A-3C illustrate examples of various PVC types in ECG tracings recorded from patients, such as a PVC singleton 310, a PVC couplet 320, a PVC triplet 330 (three consecutive PVCs), or a non-sustained VT 340 comprising a train of consecutive PVCs. The processor circuit 220 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The processor circuit 220 may include circuit sets comprising one or more other circuits or sub-circuits, including a beat detector 221, a PVC candidate identifier 222, a feature extractor 224, a PVC classifier 226, a classification model selector 227, and a PVC burden estimator 228. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The beat detector 221 can detect a heartbeat using one or more physiologic signals sensed by the sensor circuit 210. In an example, the sensor circuit 210 may be coupled to one or more implantable, wearable, or otherwise ambulatory cardiac activity sensors configured to sense cardiac electrical or mechanical activity from the patient. In another example, physiologic signals sensed by the sensor circuit 210 may be stored in a storage device such as an electronic medical record system. The beat detector 221 may receive a physiologic signal from the storage device, such as in response to a user command or a trigger event, and detect heartbeats using the received physiological signal.

The beat detector 221 can detect heartbeats from a cardiac electrical signal, such as an ECG sensed using surface electrodes or subcutaneous electrodes, or intracardiac EGM sensed from inside the heart chamber or heart tissue using intracardiac electrodes. The heartbeat thus detected can correspond to a QRS complex in a ECG or EGM that represents a ventricular depolarization. In another example, heartbeats can be detected from a cardiac mechanical signal, such as a heart sounds (HS) signal such as sensed using an accelerometer or a microphone to sense cardiac vibrational or acoustic information, a cardiac impedance signal that varies with cyclic cardiac contractions which may be sensed using an impedance sensor, or a pressure signal that varies with arterial pulses which may be sensed using a pressure sensor, among others.

In some examples, the beat detector 221 may preprocess the received physiological signal to improve the signal quality, and detect heartbeats from the pre-processed signal. The preprocessing may include signal filtering to improve a signal-to-noise ratio. In an example, the beat detector 221 may determine a noise characteristic, such as a noise level, of the sensed cardiac electrical signal within a noise window, and filter the sensed cardiac electrical signal using the detected noise level. In an example, the beat detector 221 may use an adaptive filter to cancel or attenuate the noise iteratively. may then be detected from the filtered signal.

The detected heartbeats can be screened by the PVC candidate identifier 222 to identify PVC candidates, a process referred to as a trigger stage of tiered PVC detection in this document. During the trigger stage, the PVC candidate identifier 222 can identify, from the detected heartbeats, a PVC candidate of one or more types using signal characteristics of the detected heartbeats, such as signal amplitudes, or cardiac intervals between detected heartbeats, among others. In an example, the cardiac interval check can include identifying a compensatory pause pattern, characterized by a consecutive "short-long" interval pattern comprising a shortened pre-PVC interval shorter than a baseline cycle length (e.g., during normal sinus rhythm, or NSR) followed by a prolonged post-PVC interval longer than the baseline cycle length. In an example, the PVC candidate identifier 222 can identify from the received heartbeats one or more of a PVC singleton candidate 222A, a PVC couplet candidate 222B, or a PVC run candidate 222C using signal amplitudes or cardiac intervals of the detected heartbeats, among others features. Identification of PVC candidates of specific types or patterns can help improve efficiency the accuracy of subsequent PVC confirmation and classification as done by the PVC classifier 226. Examples of the trigger stage PVC candidate identification are discussed below with reference to FIG. 4.

In some examples, the PVC candidate identifier 222 may initially identify a unified PVC couplet/PVC run candidate without distinguishing between a PVC couplet candidate and a PVC run candidate. When a PVC couplet is confirmed by the PVC classifier 226, the PVC candidate identifier 222 may further identify a PVC run candidate based on signal characteristics of the heartbeat immediately following a confirmed PVC couplet (the "post-couplet heartbeat"). Examples of such delayed trigger for PVC run candidate are discussed below with reference to FIG. 5.

The identified PVC candidates can be confirmed and further classified as one of PVC types, such as a PVC singleton, a PVC couplet, or a PVC run (also referred to as a non-sustained VT, or NSVT, in this document), a process referred to as a confirmation stage of the tiered PVC detection in this document. During the confirmation stage, the feature extractor 224 can extract a set of features from the identified PVC candidate. Such features may be used to confirm and classify the PVC candidates by the PVC classifier 226. Compared to signal characteristics (e.g., signal amplitude and intervals between heartbeats) used by the PVC candidate identifier 222 for identifying PVC candidates, the feature extractor 224 may extract more sophisticated features including, for example, one or more amplitude-based features, interval-based features, or morphology-based features of the heartbeats. Using such more sophisticated features can help reduce classification error during the confirmation stage. On the other hand, because the first trigger stage (of identifying PVC candidates) requires less resources and consumes less power than the second confirmation stage (of confirming and classifying PVC candidates), the tiered PVC detection discussed herein can make efficient use of system resources, reduce power consumption, and better meet device longevity requirements in an implantable medical device. Examples of amplitude-based features may include a ratio of a peak-to-peak (PP) amplitudes between two consecutive heartbeats (e.g., between the present beat and its immediate preceding beat, or between the present beat and its immediate following beat), or a ratio of PP amplitudes measured in two distinct frequency bands. Examples of interval-based features may include a difference of cardiac intervals between two consecutive heartbeats in the received cardiac signal (e.g., between the present beat and its immediate preceding beat, or between the present beat and its immediate following beat), expected compensatory pause difference. Examples of morphology-based features may include a morphological similarity metric between two heartbeats, or between a heartbeat and a pre-generated template beat morphology, such as on generated from heartbeats during a normal sinus rhythm (NSR) and thus referred to as a "NSR template." In an example, a correlation waveform analysis (CWA) can be used to compute the similarity metric as a correlation between morphological features of a heartbeat and morphological features of a NSR template. In another example, a dynamic correlation waveform analysis (DCWA) can be used to compute the similarity metric as a correlation between respective morphological features of two consecutive heartbeats (without using NSR template). In an example, the morphology features may include a QRS width, or QRS area under the curve derived from the ECG or EGM signal portions of a heartbeat.

In some examples, the feature extractor 224 can extract a set of features according to the type of the identified PVC candidate. For example, the feature extractor 224 may extract a set of singleton features 224A for the identified PVC singleton candidate 222A, a set of couplet features 224B for the identified PVC couplet candidate 222B, or a set of PVC run features 224C for the identified PVC run candidate 222C. The features for one type of PVC candidate may be different from the features for another type of PVC candidate. For example, the two feature sets may have different number or type of features, such as amplitude-based features, interval-based features, or morphology-based features. In an example, the couplet features 224B may include two separate feature sets (referred to as couplet-1 features and couplet-2 features) respectively generated for the two consecutive PVCs in an identified PVC couplet candidate. The couplet-1 features and couplet-2 features may be different from each other (e.g., they may have different number or type of features, such as amplitude-based features, interval-based features, or morphology-based features). In an example, the couplet-1 features and couplet-2 features may each be different from the singleton features 224A. In an example where the PVC run candidate 222C is determined based on the delayed trigger as stated above (that is, identifying another PVC beat immediately following a confirmed PVC couplet, the "post-couplet heartbeat"), the feature extractor 224 can generate the PVC run features 224C including features extracted from the post-couplet heartbeat.

The PVC classifier 226 can confirm and classify the PVC candidates using the PVC candidates features extracted by the feature extractor 224. In an example, the PVC classifier 226 may include separate detectors for confirming different types of PVC candidates using the respective features generated by the feature extractor 224, including, for example, a singleton detector 226A to confirm the singleton candidate 222A using the singleton features 224A, a couplet detector 226B to confirm the couplet candidate 222B using the couplet features 224B, or a PVC run detector 226C to confirm the PVC run candidate 222C using the PVC run features 224C.

In an example, the PVC classifier 226 (or any of the detectors 226A-226C), may confirm and classify the PVC candidate using at least one trained computational model. The at least one computational model can be generated using a model generator circuit, which can be included in the processor circuit 220 or separated from the processor circuit 220. The at least one computational model can be trained to confirm and classify a PVC type (e.g., singleton, couplet, or PVC run) for any given PVC candidate. In some examples, the at least one computational model may further be trained to identify respective feature sets 224A-224C for different types of PVC candidates 222A-222C. The feature extractor 224 may use the at least one trained computational model to extract features from the signal portions corresponding to the PVC candidates.

In an example, the at least one trained computational model can include a machine learning (ML) model. The ML model may be trained using supervised learning or unsupervised learning. Supervised learning uses prior knowledge (e.g., examples that correlate inputs to outputs or outcomes) to learn the relationships between the inputs and the outputs. The goal of supervised learning is to learn a function that, given some training dataset, best approximates the relationship between the training inputs and outputs so that the ML model can implement the same relationships when given inputs to generate the corresponding outputs. Unsupervised learning is the training of an ML algorithm using information that is neither classified nor labeled, and allowing the algorithm to act on that information without guidance. Unsupervised learning is useful in exploratory analysis because it can automatically identify structure in data. Examples of the ML model may include logistic regression, Naive-Bayes, Random Forest (RF), neural networks (NN), matrix factorization, or Support Vector Machines (SVM), among others. In an example, the ML model has an architecture of a deep neural network Examples of DNN include a convolutional neural network (CNN), a recurrent neural network (RAN), a deep belief network (DBN), a long-term and short-term memory (LSTM) network, a transfer learning network, or a hybrid neural network comprising two or more neural network models of different types or different model configurations.

By way of example and not limitation, the at least one trained computational model can include at least one trained logistic regression (LG) model comprising respective weight factors for the set of features generated by the feature extractor 224. The PVC classifier 226 (or any of the detectors 226A-226C) can use the at least one trained LG model to compute a weighted combination of the set of features each weighted by the respective weight factors, and classify the PVC candidate based on a comparison of the weighted combination to a confidence threshold. By way of example and not limitation, the singleton detector 226A can apply a signal portion (e.g., ECG or EGM) of the identified PVC singleton candidate 222A to a trained singleton detection model (e.g., an LG model), and confirm a detection of PVC singleton when the weighted sum of the singleton features 224A exceeds a first confidence threshold. Similarly, the couplet detector 226B can apply a signal portion of the identified PVC couplet candidate 222B to a trained couplet detection model (e.g., an LG model), and confirm a detection of PVC couplet when the weighted sum of the couplet features 224B exceeds a second confidence threshold. The PVC run detector 226C can apply a signal portion of the identified PVC run candidate 222C to a trained PVC run detection model (e.g., an LG model), and confirm a detection of PVC run when the weighted sum of the PVC run features 224C exceeds a third confidence threshold. The first, second, and third confidence thresholds can be different from each other, and determined during model training.

In an example, the couplet detector 226B can confirm the couplet candidate 222B by separately confirming each of the two consecutive PVCs (couplet-1 and couplet-2) in the identified PVC couplet candidate. The couplet detector 226B can apply a signal portion of couplet-1 to a first trained computational model (e.g., an LG model) to identify a feature set (couplet-1 features as discussed above), and to confirm the detection of couplet-1. Similarly, the couplet detector 226B can apply a signal portion of couplet-2 to a second trained computational model (e.g., an LG model) to identify a feature set (couplet-2 features as discussed above), and to confirm the detection of couplet-2.

In some examples, confirmation or classification of a PVC type (e.g., PVC couplet or PVC run) may be based on the confirmed detection another PVC type. In an example, in response to a confirmed detection of a PVC singleton by the singleton detector 226A, the couplet detector 226B can apply a signal portion of a heartbeat immediately following the confirmed PVC singleton (the "post-singleton heart- beat") to a trained computational model (e.g., an LG model) to identify a feature set from the post-singleton heartbeat, and to detect a post-singleton PVC if the model output exceeds a confidence threshold. The couplet detector 226B can then confirm the detection of a PVC couplet comprising the confirmed PVC singleton and the detected post-singleton PVC. In another example, in response to a confirmed detection of a PVC couplet by the couplet detector 226B, the PVC run detector 226C can apply a signal portion of a heartbeat immediately following the confirmed PVC couplet (the "post-couplet heartbeat") to a trained computational model (e.g., an LG model) to identify a feature set from the post-couplet heartbeat, and to detect a post-couplet PVC if the model output exceeds a confidence threshold. The PVC run detector 226C can then confirm the detection of a PVC run comprising the confirmed PVC couplet and the detected post-couplet PVC. Examples of confirming or classifying a PVC candidate are discussed below with reference to FIG. 5.

In some examples, the PVC classifier 226 (or any of the detectors 226A-226C) can apply a different trained compu- tational models to detect a particular type of PVC in response to a change in patient condition. The different trained computational models may include different respec- tive PVC features (e.g., singleton features, couplet features, or PVC run features), model architecture, or model param- eters (e.g., weight factors for respective PVC feature, and confidence thresholds, for an LG model). For example, features used in correlation waveform analysis (CWA), such as correlations between morphological features of a heart- beat and morphological features of a NSR template (a heartbeat during NSR), can be strong discriminators for PVCs. This is under the assumption that the NSR template represents NSR beats. In cases where the NSR morphology varies acutely (such as due to posture or rate-dependent factors), a lowered CWA score on NSR beats can result in false positives on non-PVC beats such as premature atrial contractions (PACs) or other shortened intervals. An NSR qualification check can help decide whether the NSR tem- plate and CWA-based features can be used for PVC detec- tion without introducing excessive false positive detections. If the NSR morphology is deemed to have changed or become unstable, an alternative set of features (excluding the CWA-based features) may be used instead to confirm and classify PVC candidates. For example, if the detected change in NSR morphology is below a change threshold, then both the CWA-based features and DCWA-based fea- tures may be used to confirm and classify the PVC candi- dates. If the detected change in NSR morphology exceeds the change threshold, then CW-based features are excluded from, and DCWA-based features are included in, the process of confirming and classifying the PVC candidates.

The classification model selector 227 can select a trained computational model for use by the feature extractor 224 and the PVC classifier 226. In some examples, the classifi- cation model selector 227 can detect a change in patient baseline condition, such as a change in NSR characteristics, and select the trained computational model for the feature extractor 224 and the PVC classifier 226 based at least on the detected change in patient baseline condition. The change in patient baseline condition, such as a change in NSR char- acteristics, can be detected periodically, or in response to a trigger event such as change in posture or physical activity as detected by a posture/activity sensor such as an acceler- ometer. Such periodic or event-triggered NSR qualification check and NSR template update are more computationally efficient than a continuous NSR qualification check and NSR template update. Examples of selecting a PVC detec- tion model based on a change in NSR characteristics are discussed below with reference to FIG. 6.

The tiered PVC detection as described above includes a trigger stage of identifying PVC candidates using signal amplitudes or cardiac intervals of the detected heartbeats, and a confirmation stage of confirming and classifying the PVC candidate as one of PVC types using features including morphology based features. As morphology based PVC detection generally requires more system resources and consumes more power, it can be challenging to meet the power consumption requirements in an implantable medical device. To reduce power consumption in the implantable medical device, in some examples, the arrhythmia detection system 200 can operate in different PVC detection modes with different computation complexity and power require- ments. In an example, a first detection mode can involve computation and power intensive morphology based fea- tures, such as the tiered PVC detection as described above. A different second detection mode can involve simpler features such as cardiac intervals and/or the signal ampli- tudes, but not morphology features. The arrhythmia detec- tion system 200 can detect PVC under the first detection mode, and transition to the second detection modes in response to a mode-switching trigger event, such as a passage of a threshold time after the detection of PVC under the first detection mode. By way of example and not limitation, the threshold time can be one week, two weeks, or other time duration as specified by the user. In some examples, the transition from the first detection mode to the second detection mode can be based on patient condition such as a risk of cardiac events (e.g., arrhythmias), or PVC burden estimate based on PVC detections under the first detection mode. Because the second detection mode gener- ally requires less computation and power consumption than the first detection mode, automatically transitioning to the second detection model can help save battery power of an implantable medical device and extend device longevity.

The PVC burden estimator 228 can generate a PVC burden estimate using the confirmed and classified PVCs of various types provided by the PVC classifier 226. The PVC burden represents a frequency of PVCs of any type detected within a specific time period, such as a 24-hour period in one example, or trend of 24-hour burden over many days. The PVC burden can be computed as a percentage of heartbeats being classified as PVCs of any type. In some examples, the PVC burden estimator 228 can generate a PVC burden specific to a particular PVC type, such as a PVC singleton burden, a PVC couplet burden, or a PVC run burden.

The user interface unit 230 may include an input device and an output device. In an example, at least a portion of the user interface unit 230 may be implemented in the external system 105. The input device may receive a user's program- ming input, such as parameters for detecting heartbeats, or user modification of model parameters in association with PVC candidate identification, feature extraction, or PVC classification. The input device may include a keyboard, on-screen keyboard, mouse, trackball, touchpad, touch- screen, or other pointing or navigating devices. The input device may enable a system user to program the parameters used for sensing the physiologic signals, detecting the arrhythmias, and generating alerts, among others. The output device may include a display to present a human-perceptible presentation of the detected PVCs and PVC burden estimate, among other information such as sensed physiologic information and detected heartbeats. The output unit may include a printer for printing hard copies of the detection information. The information may be presented in a table, a chart, a diagram, or any other types of textual, tabular, or graphical presentation formats. The presentation of the output information may include audio or other media format to alert the system user of the detected arrhythmic events. In an example, the output device may generate alerts, alarms, emergency calls, or other forms of warnings to signal the system user about the detected PVCs.

The optional therapy circuit 240 may be configured to deliver a therapy to the patient in response to the detected PVC, or the PVC burden estimate. Examples of the therapy may include electrostimulation therapy delivered to the heart, a nerve tissue, other target tissues, a cardioversion therapy, a defibrillation therapy, or drug therapy. In some examples, the therapy circuit 240 may modify an existing therapy, such as adjust a stimulation parameter or drug dosage.

In some examples, the detected PVC or the PVC burden estimate may be provided to a system component executing a process such as detecting other physiological events (e.g., arrhythmias such as atrial fibrillation or ventricular tachycardia), estimating patient cardiac risk, or generating other diagnostics. For example, a high PVC burden can trigger detection of atrial fibrillation or ventricular tachycardia, or an adjustment of a parameter of detection algorithm such as to make the algorithm more sensitive or specific to certain arrhythmias. In some examples, information such as a known cardiac risk or an early sign of a cardiac event may trigger PVC detection and PVC burden estimation. For example, a history of atrial fibrillation or a prediction of an impending arrhythmia episode may trigger PVC detection and PVC burden estimation, or an adjustment of a PVC detection algorithm such as to make it more sensitive to certain types of PVC.

Figure 4:
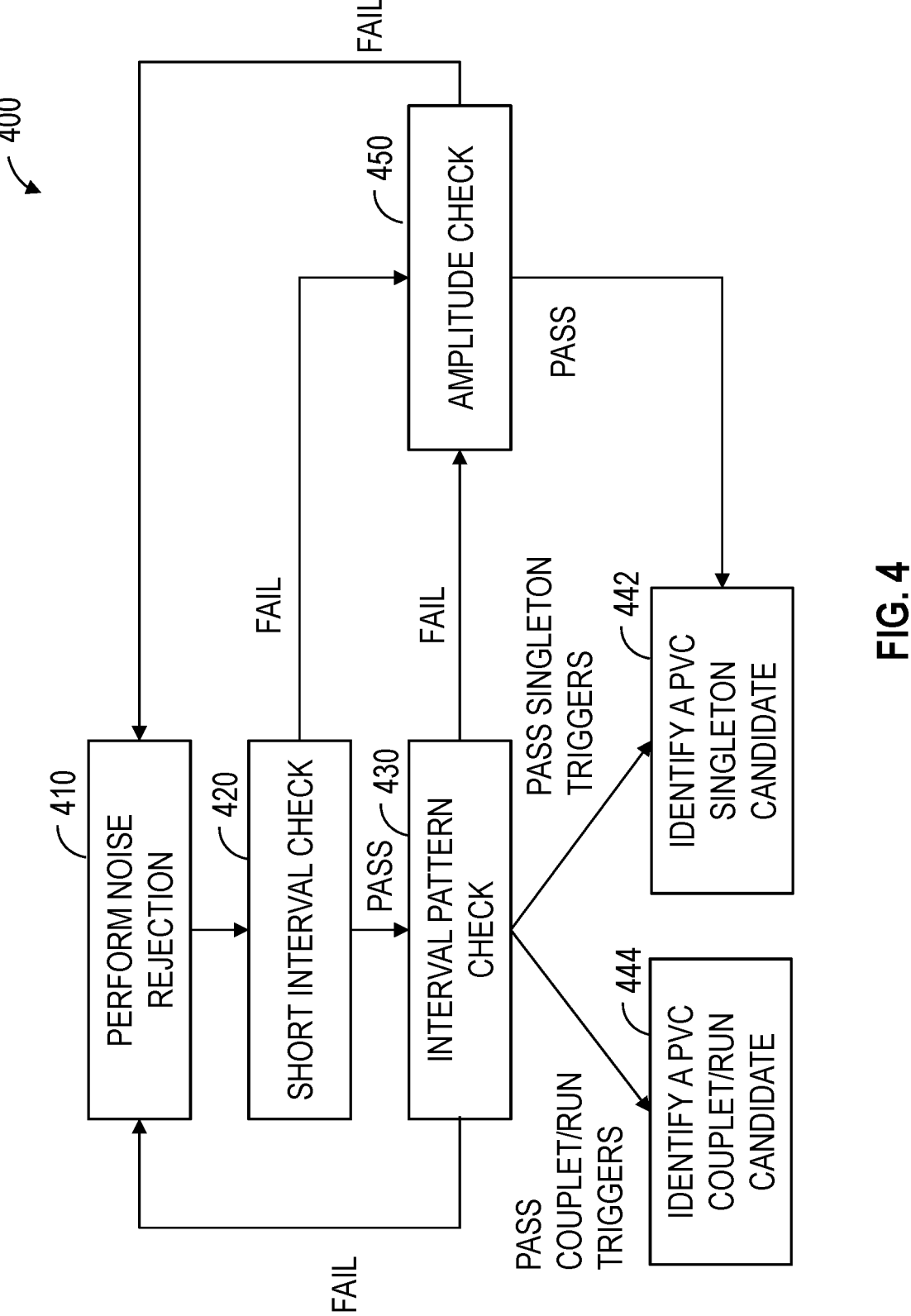
FIG. 4 is a diagram illustrating a method of identifying PVC candidates of various types from sensed heartbeats in a trigger stage of tiered PVC detection.

FIG. 4 is a diagram illustrating a method 400 of identifying PVC candidates of various types from sensed heartbeats in a trigger stage of a tiered PVC detection process. The method 400 may be implemented in and executed by the PVC candidate identifier 222. At 410, a physiological signal (e.g., ECG or EGM) from which the heartbeats are detected can be pre-processed to reject noisy intervals and heartbeats with very low amplitude (such as below an amplitude threshold). At 420, the pre-processed signal can be checked for a shortened interval, such as shorter than a baseline cardiac interval during NSR by a specific margin. A shortened cardiac interval is an indication of presence of PVC. If a shortened interval is detected at 420, then at 430 an interval pattern is checked against criteria for triggering identification of a PVC singleton candidate, and against criteria for triggering identification of a PVC couplet/run candidate. The criteria for triggering PVC singleton candidate identification can include a compensatory pause pattern, characterized by a prolonged post-ectopic compensatory pause (such that the shortened interval and the prolonged compensatory interval add up to about twice the pre-ectopic or baseline cardiac interval), or a longer (but not strictly compensatory) post-ectopic interval pattern. Additionally or alternatively, the criteria for triggering PVC singleton candidate may include a difference, or a ratio, between consecutive cardiac intervals exceeding a threshold indicating the pattern of a shortened pre-ectopic interval followed by a prolonged post-ectopic interval. A PVC singleton candidate can be identified at 442 if the criteria for triggering PVC singleton candidate are met. The PVC singleton candidate can be subsequently confirmed using the singleton detector 226A.

The criteria for triggering PVC couplet/run identification can include a fast beat pairs at around twice the previous (pre-ectopic) or baseline cardiac interval, or a "slow-fast-fast" beat pattern indicating a couplet with a longer first interval and shortened second and third intervals. A PVC couplet/run candidate can be identified at 444 if the criteria for triggering PVC couplet/run candidate are met. The PVC couplet/run candidate can be subsequently confirmed and classified as a PVC couplet or a PVC run using the couplet detector 226B or the PVC run detector 226C, respectively.

If either the short interval check at 420 or the interval pattern check at 430 fails, then at 450 an amplitude check can be performed. This stage flags beats with obvious amplitude differences relative to the previous beat, with constraints placed for possibly over-sensed adjacent detections. In an example, the amplitude check at 450 can include an interval stage that uses an average cardiac cycle calculation instead of the previous interval for interval comparison. This handles cases of single PVCs in the context of very irregular cardiac intervals, such as during atrial tachyarrhythmia (e.g., atrial fibrillation or atrial flutter), when previous intervals can be very short. If the heartbeat passes the amplitude check, then a PVC singleton candidate can be identified at 442, which can subsequently be confirmed using the singleton detector 226A.

Figure 5:
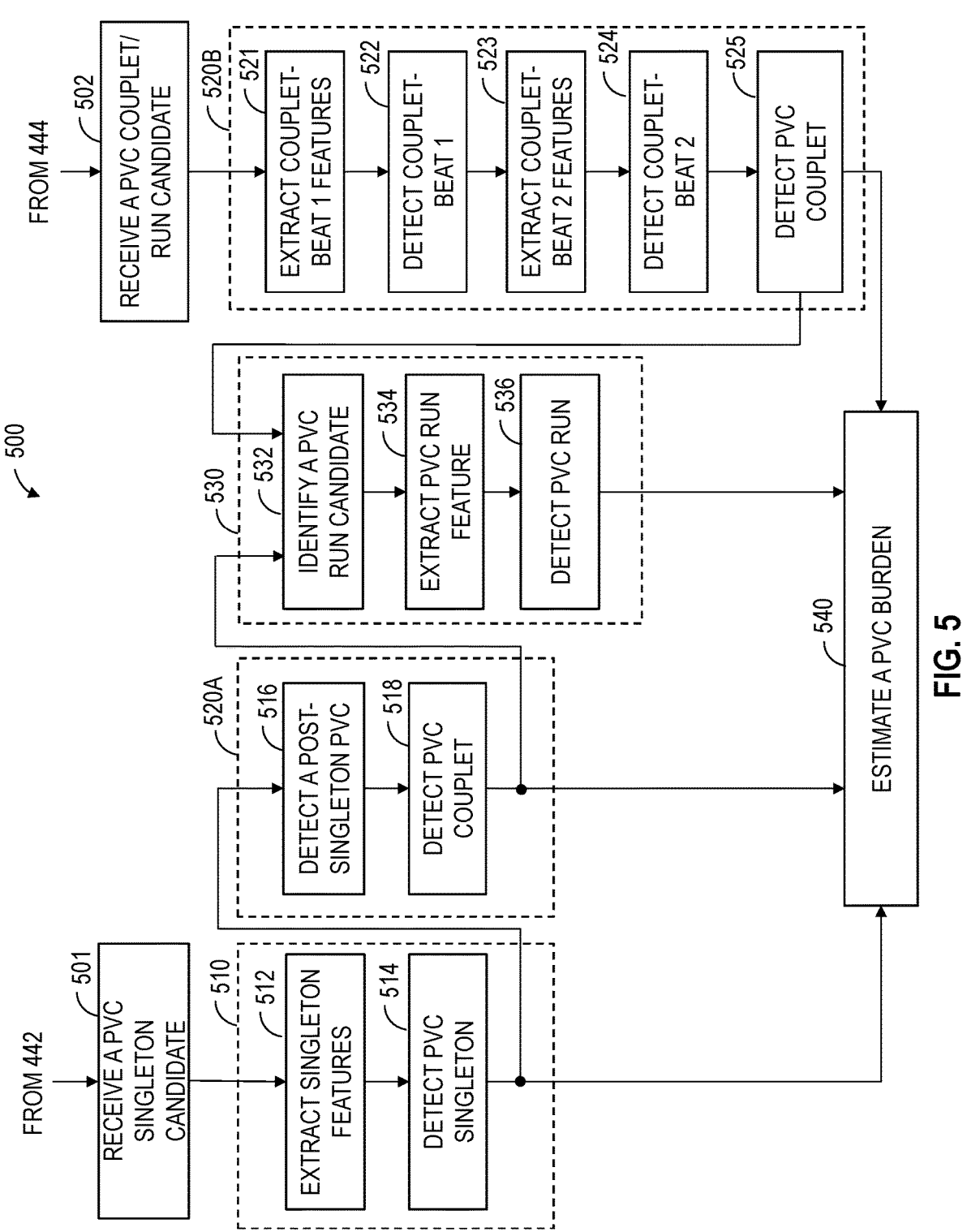
FIG. 5 is a diagram illustrating a method of confirming or classifying a PVC candidate as one of PVC types in a confirmation stage of tiered PVC detection.

FIG. 5 is a diagram illustrating a method 500 of confirming or classifying a PVC candidate, such that a PVC singleton candidate or a PVC couplet/run candidate such as those identified using the method 400, as one of PVC types in a confirmation stage of tiered PVC detection process. The method 500 can include one or more processes 510 for detecting a PVC singleton, 520A and 520B for detecting a PVC couplet, and 530 for detecting a PVC run of three or more PVCs. The method 500 can be implemented in and executed by the feature extractor 224 and the PVC classifier 226.

The method 500 begins at 501 for receiving a PVC singleton candidate such as produced at step 442 of method 400, or at step 502 for receiving a PVC couplet/run candidate such as produced at step 444 of method 400. For the PVC singleton candidate received at 501, the PVC singleton detection process 510 includes extracting a set of singleton features at 512 using, for example, the feature extractor 224. Examples of the singleton features can include amplitude-based features such as a ratio of peak-to-peak (PP) amplitudes measured in two distinct frequency bands, and morphology-based features such as CWA-based features (e.g., correlation between morphological features of a heartbeat and morphological features of a NSR template) or DCWA-based features (e.g., correlation between respective morphological features of two consecutive heartbeats). At 514, a PVC singleton can be detected using the singleton detector 226A. In an example, a signal portion (e.g., ECG or EGM) of the received PVC singleton candidate can be applied to a trained singleton detection model (e.g., an LG model) to extract the singleton features at 512, and to confirm the PVC singleton at 514 when the weighted sum of the singleton features exceeds a first confidence threshold.

The detected PVC singleton at 514 may then be used in a PVC couplet detection process 516 for detecting a PVC couplet, such as using the couplet detector 226B. At 516, a signal portion of a heartbeat immediately following the detected PVC singleton (the "post-singleton heartbeat") can be applied to a trained computational model (e.g., an LG model) to identify a feature set from the post-singleton heartbeat. The features extracted can include, for example, DCWA-based morphology features and CWA-based morphology features, among other features. A post-singleton PVC is detected if the model output exceeds a confidence threshold. At 518, a PVC couplet comprising the PVC singleton detected at 514 and the subsequent post-singleton PVC detected at 516 is detected.

The detected PVC couplet at 518 may further be used in a PVC run detection process 530 for detecting a PVC run of three or more PVCs, such as using the PVC run detector 226C. At 532, a PVC run candidate can be identified based on an analysis of the signal characteristics of the heartbeat immediately following the PVC couplet (the "post-couplet heartbeat") detected at 518. The analysis of the signal characteristics may include an consistency of cardiac intervals RR interval. If the post-couplet heartbeat satisfies an interval consistency condition, a PVC run candidate is deemed detected. At 534, a signal portion of the "post-couplet heartbeat" can be applied to a trained computational model (e.g., an LG model) to identify a feature set from the post-couplet heartbeat. The PVC run features extracted can include, for example, CWA-based morphology features, a ratio of PP amplitudes measured in two distinct frequency bands, QRS width, or interval-based features such as difference of two consecutive cardiac intervals, among other features. A post-couplet PVC is detected if the model output exceeds a confidence threshold. At 536, a PVC run comprising the PVC couplet detected at 518 and the subsequently detected post-couplet PVC is detected.

For the PVC couplet/run candidate received at 502 that comprises two consecutive PVC candidates (couplet-1 and couplet-2), a PVC couplet detection process 520B can include extracting features from couplet-1 of the PVC couplet candidate at 521, applying a signal portion of couplet-1 to a first trained computational model (e.g., an LG model) to confirm the detection of couplet-1 at 522, extracting features from couplet-2 of the PVC couplet candidate at 523, applying a signal portion of couplet-2 to a second trained computational model (e.g., an LG model) to confirm the detection of couplet-2 at 524. The couplet-1 features and couplet-2 features may be different from each other (e.g., they may have different number or type of features, such as amplitude-based features, interval-based features, or morphology-based features). With both couplet-1 and couplet-2 being confirmed as PVCs, at 525 a PVC couplet is deemed detected.

The PVC couplet detected at 525, although detected using a different process 520B than the PVC couplet obtained at 518 through the process 520A, may similarly be used in the PVC run detection process 530 for detecting a PVC run of three or more PVCs, as stated above. The resultant PVC run detected at 536 comprises the PVC couplet detected at 525 and the subsequently detected post-couplet PVC.

The PVC singlet detected at 514, the PVC couplet detected at 518 and 525, and the PVC run detected at 536, can then be used to determine a PVC burden estimate at 540, such as using the PVC burden estimator 228, as stated above with reference to FIG. 2. To avoid repeated counting of PVC events, if a PVC singleton detected at 514 is identified to be a leading PVC of a PVC couplet detected at 518, and the PVC couplet at 518 is not identified as a portion of the PVC run detected at 536, then the PVC couplet at 518, but not the PVC singleton at 514, is counted towards the PVC burden estimate at 540. Similarly, if a PVC couplet detected at 518 or at 525 are further identified as a portion of the PVC run detected at 536, then only the PVC run at 536, but not the PVC couplet at 518 or at 525, is counted towards the PVC burden estimate at 540. The PVC burden estimate can be provided to a user, such as displayed on a display of the user interface unit 230. In an example, based on the determined PVC burden, an alert or a recommendation for further evaluation or treatment can be presented to the user. In some examples, a therapy can be initiated or adjusted in response to the detected PVC, or the PVC burden estimate.

Figure 6:
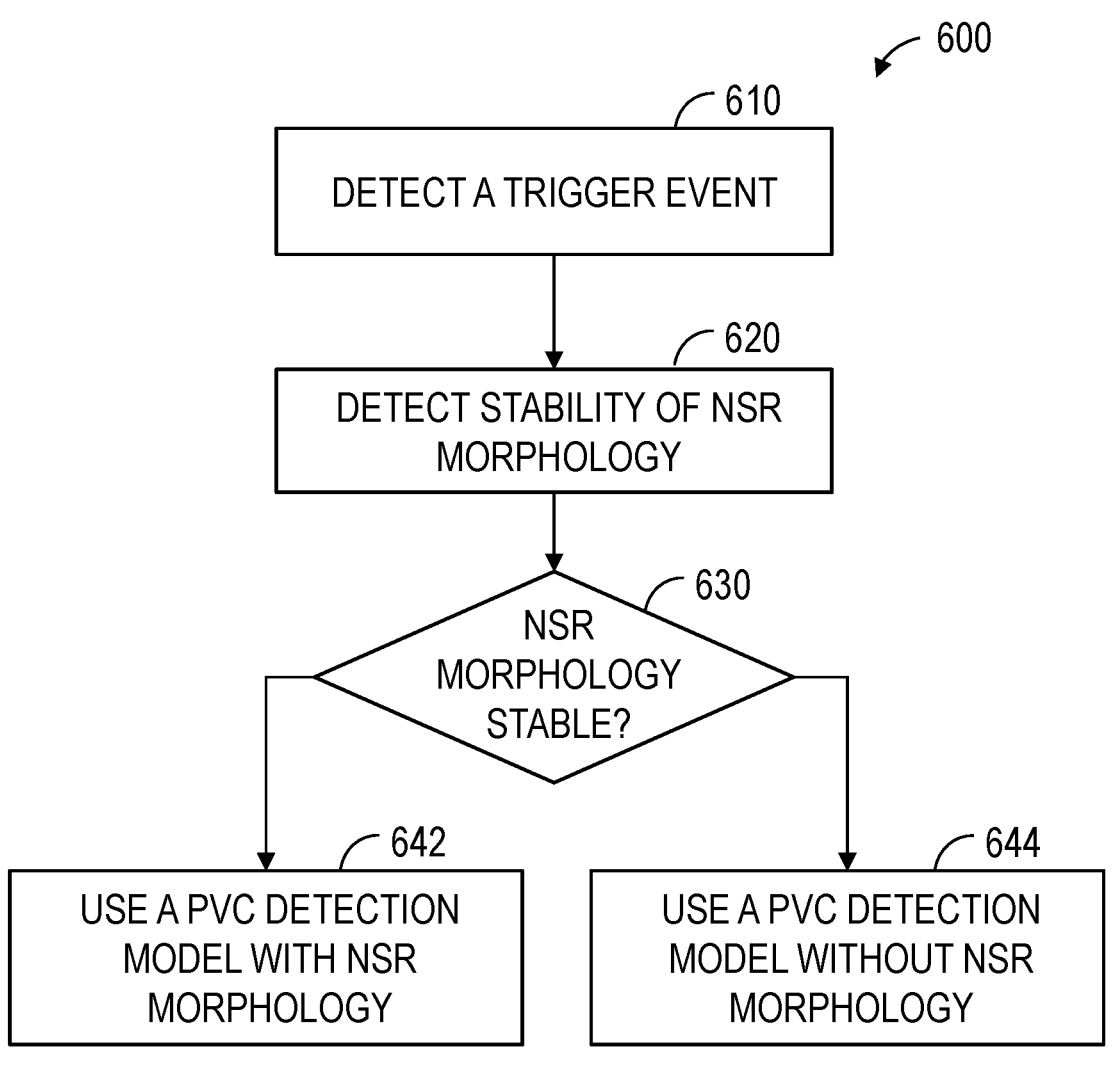
FIG. 6 is a diagram illustrating a method of selecting a PVC detection model based on a change in patient condition.

FIG. 6 is a diagram illustrating a method 600 of selecting a PVC detection model based on a change in patient condition, such as a NSR morphology. The method 600 can be implemented in an executed by the classification model selector 227.

At 610, a trigger event such as a change in posture or physical activity can be detected. At 620, in response to the detected trigger event, a stability of NSR morphology can be detected, such as by using correlations between a previously generated NSR template and a plurality of NSR beats prior to the present PVC candidate. In an example, the stability of NSR morphology can be determined using an average of the correlations.

At 630, the NSR stability can be compared to a threshold to decide if NSR is stable (i.e., no substantial change in NSR morphology). If the average correlation exceeds a threshold, a stable NSR morphology is indicated. At 642, a computational model that utilizes NSR morphology, such as CWA-based features (e.g., correlation between morphological features of a heartbeat and morphological features of a NSR template), can be used by the PVC classifier 226 (or any of the detectors 226A-226C) to confirm and classify a PVC candidate. In some examples, in addition to the CWA-based features, DCWA-based features (e.g., correlation between respective morphological features of two consecutive heartbeats) may also be included in the computational model at 642. However, if the average correlation falls below a threshold, the NSR morphology is deemed changed substantially over time and thus unstable. At 644, NSR morphology and CWA-based features can be excluded from a computational model used by the PVC classifier 226 (or any of the detectors 226A-226C) to confirm and classify a PVC candidate. In some examples, in substitute of the CWA-based features, DCWA-based features (e.g., correlation between respective morphological features of two consecutive heartbeats) can be included in the computational model at 644.

Figure 7:
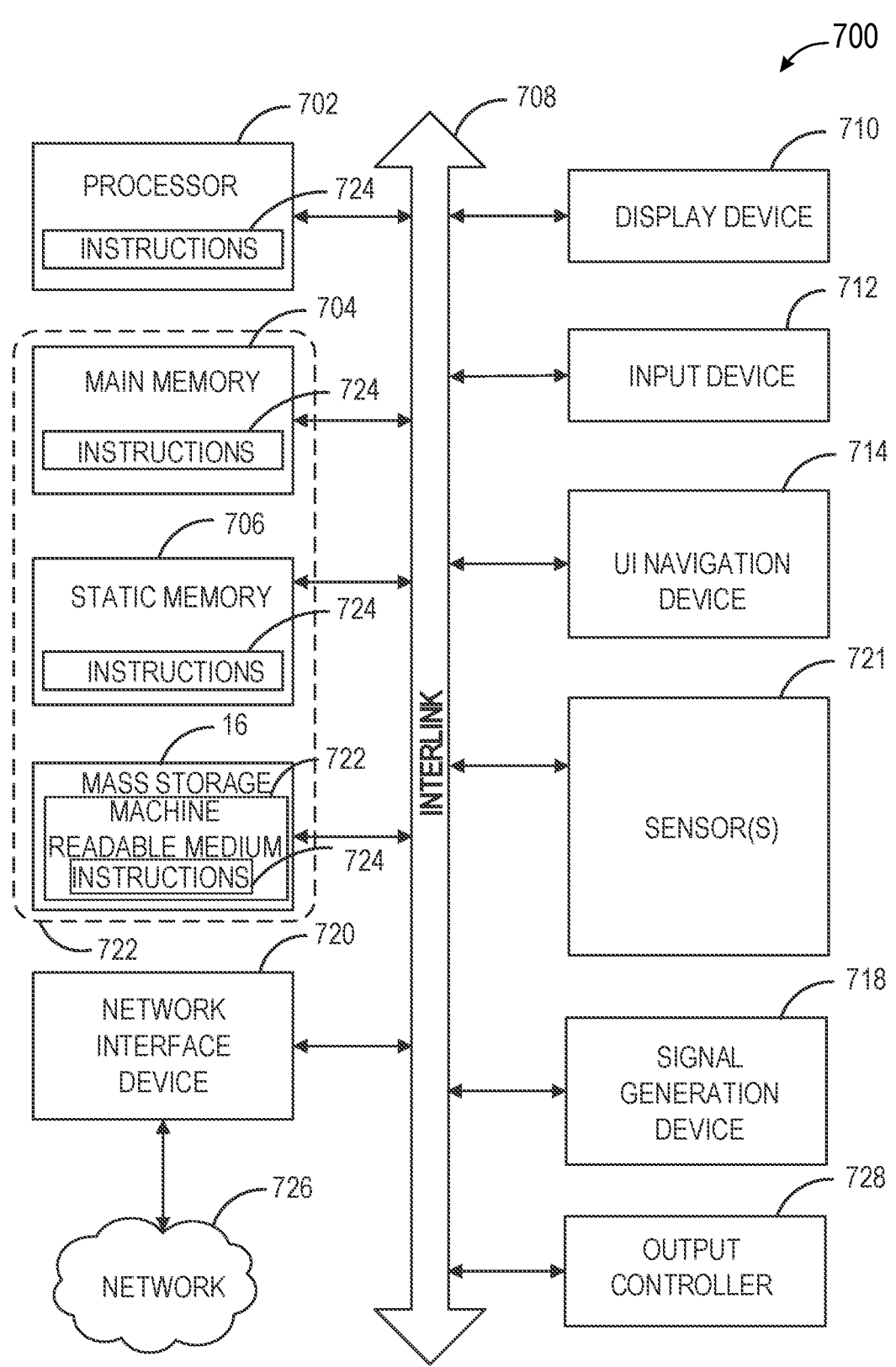
FIG. 7 illustrates generally a block diagram of an example machine upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the arrhythmia detection system 200.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine-readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine-readable media.

While the machine-readable medium 722 is illustrated as a single medium, the term "machine-readable medium" may include a single medium or multiple media (e.g., a centralized or distributed database, and/or associated caches and servers) configured to store the one or more instructions 724.

The term "machine-readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine-readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802. 11 family of standards known as WiFi®, IEEE 802. 16 family of standards known as WiMax®), IEEE 802. 15. 4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. An implantable medical device for detecting cardiac arrhythmia in a subject, comprising:
    a sensor circuit configured to sense a cardiac signal of the subject; and
    a processor circuit configured to:
        detect heartbeats from the sensed cardiac signal;
        detect a premature ventricular contraction (PVC) under a first detection mode, including to:
            identify a PVC candidate of a particular type using cardiac intervals or signal amplitudes of the detected heartbeats;
            generate a set of signal features including morphology features from the sensed cardiac signal; and
            classify the identified PVC candidate as a PVC singleton or a pattern of multiple consecutive PVCs using the generated set of signal features; and
        in response to a mode-switching trigger event, detect the PVC of the particular type under a second detection mode different than the first detection mode using the cardiac intervals or the signal amplitudes of the detected heartbeats, wherein the mode-switching trigger event includes a passage of a threshold time after the detection of PVC under the first detection mode, wherein the threshold time is a number of weeks.

2. The implantable medical device of claim 1, wherein the first detection mode includes at least one trained computational model including respective weight factors for the set of signal features, the at least one trained computational model being trained to recognize one or more PVC types.

3. The implantable medical device of claim 2, wherein the at least one trained computational model includes a logistic regression model,
    wherein to classify the identified PVC candidate under the first detection mode, the processor circuit is configured to:
        compute a weighted combination of the generated set of signal features each weighted by the respective weight factors; and
        classify the identified PVC candidate as the PVC singleton or the pattern of multiple consecutive PVCs based on a comparison of the weighted combination to a confidence threshold.

4. The implantable medical device of claim 2,
    wherein the pattern of multiple consecutive PVCs includes a PVC couplet or a PVC run of three or more consecutive PVCs;
    wherein the identified PVC candidate includes one or more of an identified PVC singleton candidate, an identified PVC couplet candidate, or an identified PVC run candidate,

26 wherein the at least one trained computational model includes one or more of a trained singleton detection model, a trained couplet detection model, or a trained PVC run detection model,
    wherein to classify the identified PVC candidate, the processor circuit is configured to apply the trained singleton detection model to the identified PVC singleton candidate, apply the trained couplet detection model to the identified PVC couplet candidate, or to apply the trained PVC run detection model to the identified PVC run candidate.

5. The implantable medical device of claim 4, wherein the processor circuit is configured to:
    identify the PVC candidate as the PVC singleton candidate; and
    apply the sensed cardiac signal to the trained singleton detection model to generate a singleton feature set for the identified PVC singleton candidate, and to confirm a PVC singleton detection using the singleton feature set and the trained singleton detection model.

6. The implantable medical device of claim 4, wherein the processor circuit is configured to:
    identify the PVC candidate as the PVC couplet candidate based on two consecutive cardiac intervals shorter than an interval threshold; and
    apply the sensed cardiac signal to the trained couplet detection model to generate first and second feature sets respectively for the two consecutive PVCs of the identified PVC couplet candidate, and to confirm a PVC couplet detection using the first and second feature sets and the trained couplet detection model.

7. The implantable medical device of claim 4, wherein the processor circuit is configured to:
    identify the PVC candidate as the PVC run candidate based on (i) three or more consecutive cardiac intervals shorter than an interval threshold, or (ii) a confirmed PVC couplet detection; and
    apply the sensed cardiac signal to the trained PVC run detection model to generate a third feature set for a third or subsequent PVC of the PVC run candidate, and to confirm a PVC run detection using the third feature set and the trained PVC run detection model.

8. The implantable medical device of claim 2, wherein the at least one trained computational model includes a logistic regression model,
    wherein to classify the identified PVC candidate under the first detection mode, the processor circuit is configured to:
        compute a weighted combination of the generated set of signal features each weighted by the respective weight factors; and
        classify the identified PVC candidate as the PVC singleton or the pattern of multiple consecutive PVCs based on a comparison of the weighted combination to a confidence threshold.

9. The implantable medical device of claim 1, wherein the set of signal features generated under the first detection mode include:
    one or more amplitude features including a ratio of a peak-to-peak (PP) amplitudes between two consecutive heartbeats in the sensed cardiac signal; or
    one or more interval features including a difference of cardiac intervals between two consecutive heartbeats in the sensed cardiac signal.

10. The implantable medical device of claim 1, wherein the set of signal features generated under the first detection mode include one or more morphology features including:

a first morphological similarity metric between (i) a heartbeat in the sensed cardiac signal and (ii) a normal sinus rhythm (NSR) morphology; or a second morphological similarity metric between two consecutive heartbeats in the sensed cardiac signal.

11. The implantable medical device of claim 10, wherein one or more of the first or the second morphological similarity metric includes a correlation metric.

12. The implantable medical device of claim 10, wherein the processor circuit is configured to:

detect a change in NSR morphology; and classify the identified PVC candidate using the first morphological similarity metric and the second morphological similarity metric if the detected change in NSR morphology is below a change threshold, and using the second morphological similarity metric but not the first morphological similarity metric if the detected change in NSR morphology exceeds the change threshold.

13. The implantable medical device of claim 1, wherein the first detection mode includes at least one trained computational model including respective weight factors for the set of signal features, the at least one trained computational model being trained to recognize one or more PVC types.

14. A method for detecting cardiac arrhythmia in a subject using an implantable medical device, comprising:

sensing a cardiac signal of the subject using a sensor circuit;

detecting heartbeats from a cardiac signal of the subject;

detecting a premature ventricular contraction (PVC) under a first detection mode, including:

identifying a PVC candidate of a particular type using cardiac intervals or signal amplitudes of the detected heartbeats;

generating a set of signal features including morphology features from the sensed cardiac signal; and classifying the identified PVC candidate as a PVC singleton or a pattern of multiple consecutive PVCs using the generated set of signal features;

in response to a mode-switching trigger event, detecting the PVC of the particular type under a second detection mode different than the first detection mode using the cardiac intervals or the signal amplitudes of the detected heartbeats, wherein the first detection mode includes at least one trained computational model including respective weight factors for the set of signal features, the at least one trained computational model being trained to recognize one or more PVC types, wherein the pattern of multiple consecutive PVCs includes a PVC couplet or a PVC run of three or more consecutive PVCs, wherein the identified PVC candidate includes one or more of an identified PVC singleton candidate, an identified PVC couplet candidate, or an identified PVC run candidate, wherein the at least one trained computational model includes one or more of a trained singleton detection model, a trained couplet detection model, or a trained PVC run detection model, wherein classifying the identified PVC candidate includes applying the trained singleton detection model to the identified PVC singleton candidate, applying the trained couplet detection model to the identified PVC couplet candidate, or applying the trained PVC run detection model to the identified PVC run candidate, wherein the method includes:

identifying the PVC candidate as the PVC singleton candidate;

applying the cardiac signal to the trained singleton detection model to generate a singleton feature set for the identified PVC singleton candidate, and to confirm a PVC singleton detection using the singleton feature set and the trained singleton detection model; and in response to the confirmed PVC singleton detection, applying the cardiac signal to a trained post-singleton PVC detection model to generate a post-singleton feature set for a heartbeat immediately following the confirmed PVC singleton, and to confirm a PVC couplet detection using the post-singleton feature set and the trained post-singleton PVC detection model.

15. The method of claim 14, wherein the mode-switching trigger event includes a passage of a threshold time after the detection of PVC under the first detection mode.

16. The method of claim 14, comprising:

identifying the PVC candidate as the PVC couplet candidate based on two consecutive cardiac intervals shorter than an interval threshold; and applying the cardiac signal to the trained couplet detection model to generate first and second feature sets respectively for the two consecutive PVCs of the identified PVC couplet candidate, and to confirm a PVC couplet detection using the first and second feature sets and the trained couplet detection model.

17. The method of claim 14, comprising:

identifying the PVC candidate as the PVC run candidate based on one or more of (i) three or more consecutive cardiac intervals shorter than an interval threshold or (ii) a confirmed PVC couplet detection; and applying the cardiac signal to the trained PVC run detection model to generate a third feature set for a third or subsequent PVC of the PVC run candidate, and to confirm a PVC run detection using the third feature set and the trained PVC run detection model.

18. An implantable medical device for detecting cardiac arrhythmia in a subject, comprising:

a sensor circuit configured to sense a cardiac signal of the subject; and a processor circuit configured to:

detect heartbeats from the sensed cardiac signal;

detect a premature ventricular contraction (PVC) under a first detection mode, including to:

identify a PVC candidate of a particular type using cardiac intervals or signal amplitudes of the detected heartbeats;

generate a set of signal features including morphology features from the sensed cardiac signal; and classify the identified PVC candidate as a PVC singleton or a pattern of multiple consecutive PVCs using the generated set of signal features; and in response to a mode-switching trigger event, detect the PVC of the particular type under a second detection mode different than the first detection mode using the cardiac intervals or the signal amplitudes of the detected heartbeats, wherein the set of signal features generated under the first detection mode include one or more morphology features including:

a first morphological similarity metric between (i) a heartbeat in the sensed cardiac signal and (ii) a normal sinus rhythm (NSR) morphology; or a second morphological similarity metric between two consecutive heartbeats in the sensed cardiac signal, wherein one or more of the first or the second morphological similarity metric includes a correlation metric, wherein the processor circuit is configured to:

detect a change in NSR morphology; and classify the identified PVC candidate using the first morphological similarity metric and the second morphological similarity metric if the detected change in NSR morphology is below a change threshold, and using the second morphological similarity metric but not the first morphological similarity metric if the detected change in NSR morphology exceeds the change threshold.

19. The implantable medical device of claim 18, wherein the mode-switching trigger event includes a passage of a threshold time after the detection of PVC under the first detection mode.

20. The implantable medical device of claim 19, wherein the threshold time is a number of weeks.

* * * * *